United States Patent [19]

Abrams et al.

[11] Patent Number: 4,671,295
[45] Date of Patent: Jun. 9, 1987

[54] METHOD FOR MEASURING CARDIAC OUTPUT

[75] Inventors: Jerome H. Abrams, Minneapolis; Claire T. Hovland, Mound, both of Minn.

[73] Assignee: Applied Biometrics, Inc., Mound, Minn.

[21] Appl. No.: 930,950

[22] Filed: Nov. 11, 1986

Related U.S. Application Data

[63] Continuation-in-part of Ser. No. 691,675, Jan. 15, 1985, abandoned.

[51] Int. Cl.$^4$ ............................................. A61B 10/00
[52] U.S. Cl. .................................... 128/663; 128/713
[58] Field of Search ....................... 128/661, 663, 713; 73/861.25

[56] References Cited

U.S. PATENT DOCUMENTS

| Re. 31,377 | 9/1983 | Mylrea | 128/715 |
|---|---|---|---|
| 3,498,290 | 3/1970 | Shaw et al. | 128/663 |
| 3,734,094 | 5/1973 | Calinog | 128/642 |
| 3,951,136 | 4/1976 | Wall | 128/642 |
| 4,304,239 | 12/1981 | Perlin | 128/642 |
| 4,304,240 | 12/1981 | Perlin | 128/671 |
| 4,316,391 | 2/1982 | Tickner | 128/663 |
| 4,349,031 | 9/1982 | Perlin | 128/642 |
| 4,354,501 | 10/1982 | Colley et al. | 128/663 |
| 4,369,794 | 1/1983 | Furler | 128/715 |
| 4,370,985 | 2/1983 | Takeichi et al. | 128/663 |
| 4,509,526 | 4/1985 | Barnes et al. | 128/713 |

OTHER PUBLICATIONS

Jethwa et al, "Blood Flow Measurements Using Ultrasonic Pulsed Random Signal Doppler System", IEEE Transactions on Sonics and Ultrasonics 1-11, Jan. 1975.
Huntsman et al, "Transcutaneous Determination of Aortic Blood-Flow", American Heart Journal, vol. 89, No. 5, 609-612, May 1975.
Kohanna et al, "Monitoring of Cardiac Output by Thermodilution After Open Heart Surgery", Journal of Thoracic and Cardiovascular Surgery, vol. 73, No. 3, pp. 451-457, 3/77.
Darsee et al, "Transcutaneous Doppler Method of Measuring Cardiac Output", American Journal of Cardiology, vol. 46, pp. 613-618, Oct. 1980.
Heneghan et al, "Non-Invasive Measurement of Cardiac Output During Anaesthesia", British Journal of Anaesthesia, vol. 53, pp. 351-355, 1981.
Hartley et al, "An Ultrasonic Pulsed Doppler System for Measuring Blood Flow in Small Vessels", Journal of Applied Physiology, vol. 37, No. 4, Oct. 1974.
Huntsman et al, "Non-Invasive Doppler Determination of Cardiac Output in Man", Circulation, vol. 67, No. 3, Mar. 1983, pp. 593-602.

(List continued on next page.)

Primary Examiner—Edward M. Coven
Assistant Examiner—Ruth S. Smith
Attorney, Agent, or Firm—Dorsey & Whitney

[57] ABSTRACT

Blood flow in the aorta and pulmonary artery of a mammal, most typically a human, is measured volumetrically by a non-invasive, ultrasound method and apparatus. The method comprises placing a piezoelectric ultrasound transducer in the trachea in great proximity to the aorta or pulmonary artery by passage through the oral or nasal cavity past the epiglottis and into the trachea or by passage through the surgical opening into the trachea in the case of patients who have had a tracheotomy. Ultrasound waves are transmitted toward the path of flow of blood in the artery. Reflected waves are received. The average Doppler frequency difference between transmitted and received waves is measured. The cross-sectional size of the artery is measured. Blood flow rate is determined from the measurements. The apparatus comprises a tracheal tube or probe with one or two transducers mounted at one end the tube. The transducer(s) is (are) disposed to transmit ultrasound in selected directions. Electrical conductors extend from the transducers the length of the probe.

14 Claims, 6 Drawing Figures

OTHER PUBLICATIONS

Keagy et al, "A Removeable Extraluminal Doppler Probe for Continuous Monitoring of Changes in Cardiac Output", Journal of Ultrasound Medicine, 2:357–362, Aug. 1983.

Baker, "Pulsed Ultrasonic Doppler Blood-Flow Sensing", IEEE Transactions on Sonics and Ultrasonics, vol. SU-17, No. 3, Jul. 1970, pp. 170–184.

Duck et al, "An Esophageal Doppler Probe for Aortic Flow Velocity Monitoring", Ultrasound in Med. & Biol., vol. 1, No. 3, pp. 233–241, Aug. 1974.

Olson et al, "A Nondestructive Ultrasonic Technique to Measure Diameter and Blood Flow in Arteries", IEEE Transactions on Biomedical Engineering, vol. BME-21, No. 2, pp. 168–171, Mar. 1974.

Histand et al, "Ultrasonic Pulsed Doppler Transoesophageal Measurement of Aortic Haemodynamics in Humans", Ultrasonics, Sep. 1979.

Wells et al, "Ultrasonic Transesophageal Measurement of Cardiac Output", 1978 Advances in Bioengineering, San Francisco, Calif., (Dec. 10–15, 1978), pp. 121–123.

Martin et al, "An Ultrasonic Catheter for Intravascular Measurement of Blood Flow", IEEE Transactions on Sonics and Ultrasonics, vol. SU-27, No. 6, Nov. 1980, pp. 277–286.

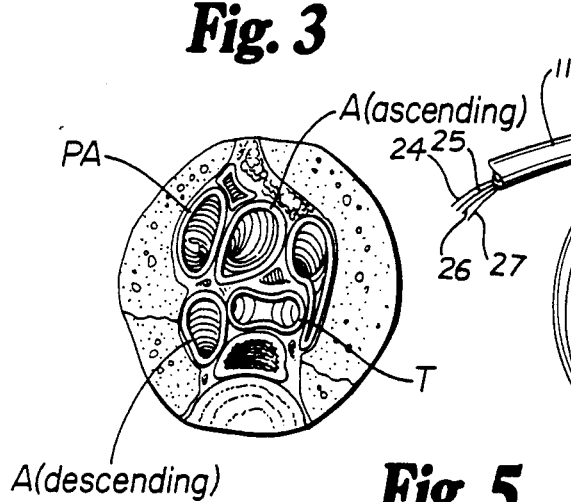
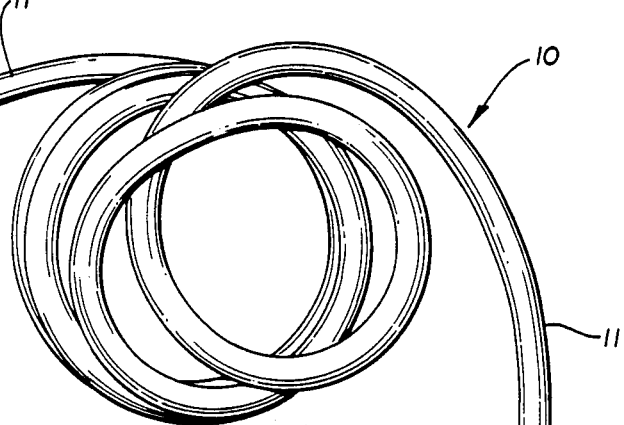
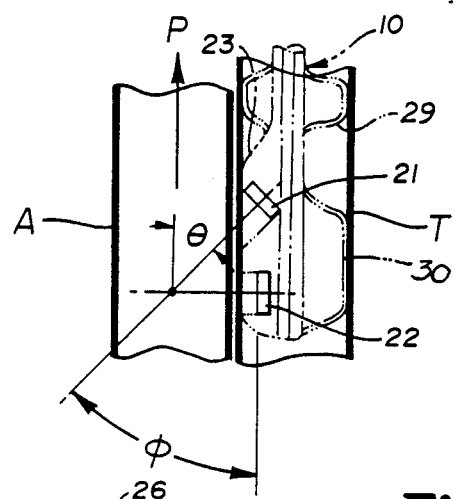
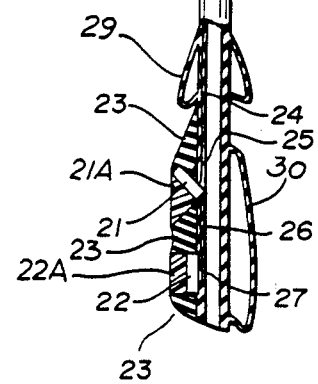
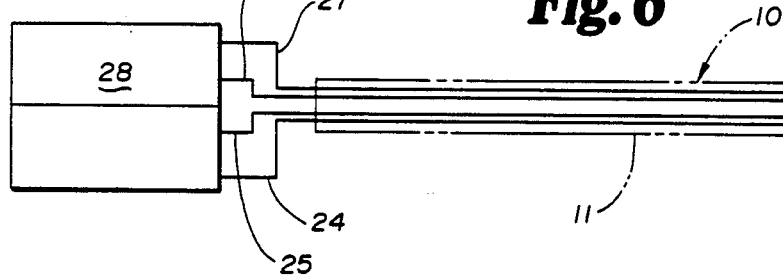
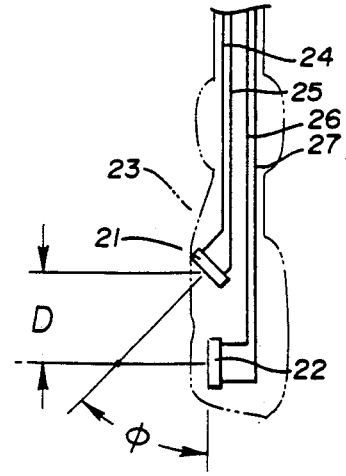

METHOD FOR MEASURING CARDIAC OUTPUT

This is a continuation-in-part of application Ser. No. 691,675, filed Jan. 15, 1985, now abandoned.

BACKGROUND OF INVENTION

1. Field of Invention

Measurement of cardiac output is crucial in the care of critically ill patients such as patients with multiple trauma, patients in overwhelming sepsis, and patients with acute myocardial infarction. In the case of patients with acute myocardial infarction, there is a worsening prognosis with decrease in cardiac output. Knowledge of the cardiac output provides information useful in determining the clinical state of a given patient and in rationally planning therapy for the patient. Such information is not contained in the usually measured vital signs. For example, a low mean arterial pressure with elevated pulse does not adequately distinguish between cardiogenic and septic shock, the treatments for which are quite different. Consequently, a method that distinguishes between cardiogenic and septic shock would be important in planning appropriate therapy. The measurement of cardiac output, in this case, would provide valuable information that would allow an appropriate diagnosis to be made.

2. Prior Art

The importance of knowing cardiac output has led to many methods for its determination. The most commonly used method in widespread clinical use is thermodilution. In the thermodilution method a catheter is placed into the central venous circulation, usually by percutaneous entry into the internal jugular or subclavian vein. A balloon at the end of the catheter is inflated, and the normal flow of blood is employed to direct the tip of the catheter into the pulmonary artery. Measurement of cardiac output is made by observing the dissipation of a temperature pulse, usually a bolus of iced sterile water or saline solution. As is evident, the method cannot be used without invasion of the vascular tree. Indeed, the catheter is threaded through the heart and the heart valves. Flow direction is not entirely reliable. In certain patients access to the pulmonary artery is impossible. During placement of the catheter cardiac arrhythmias are not uncommon. Other complications include sepsis, thrombosis of the central veins, emboli, and fatal rupture of the pulmonary artery. Other disadvantages of the technique include lack of continuous information about the cardiac output and chance location of the catheter, such as in an unfavorable pulmonary artery branch, with erroneous values for the cardiac output. Analysis of the error inherent in the measurement of blood flow by thermodilution has revealed a standard deviation of 20–30%.

Measurement of cardiac output has also been done by the indocyanine green dye technique, which suffers from several disadvantages. The technique is cumbersome, it requires the placement of an arterial catheter, is not accurate at low levels of cardiac output and is difficult to use for repeated measurements in the same patient. Complications include catheter site hematoma, sepsis from the catheter, thromboses of the artery containing the indwelling catheter, and pseudoaneurysm formation at the site of arterial puncture.

The Fick method is based on the measurement of oxygen consumption. It is best used in awake, alert, stable patients not requiring respiratory support on a ventilator. The method requires invasion of the pulmonary artery in order to obtain samples of mixed venous blood for determination of the oxygen content. Like the indocyanine green dye technique, an arterial catheter must be placed for sampling of arterial blood for oxygen content with the disadvantages mentioned above.

Transcutaneous ultrasound has also been used. Ultrasound transducers are placed externally on the body at the suprasternal notch. Under the most sanguine circumstances, at least 10% of patients cannot have their cardiac outputs measured in this way. Many difficulties with this approach have been reported: repeated measurements may lead to varying location of the sample volume that is scanned, there are changes in the angle of intersection of the ultrasound beam with the axis of the vessel, capability for continuous measurement of the cardiac output is not available, and other major thoracic vessels may interfere with the Doppler ultrasound signals. Further, the method is not feasible in many important clinical settings in which the patients are not cooperative or are in the operating room, where the suprasternal notch may not be accessible.

Because of these difficulties, an implantable, removable Doppler ultrasound device for measurement of the cardiac output has been developed for direct attachment to the aorta. The device requires a major, operative, invasive intervention, such as splitting the sternum or removal of a rib to enter the chest cavity, for placement of the device directly on the wall of the aorta. Removal of the device also requires surgical intervention. If the device were to be lost in a major body cavity, a major surgical procedure would be required.

Measurement of cardiac output by continuous or single breath, gas-washout has been attempted, but is not used in standard clinical medicine. Such methods require many approximations of lung function in modeling the system. Time consuming numerical analysis is required. In one study, measurement of cardiac output in anesthetized patients using argon and freon during passive rebreathing was shown to provide lower cardiac outputs than a simultaneously performed Fick determination. The authors concluded that the method caused significant disturbances of hemodynamics and was therefore not suitable for widespread use.

Indirect measurements include the pulse, blood pressure, and urine output, but these measurements are not specific for cardiac output. For example, in the presence of acute renal failure, urine output cannot be correlated with perfusion of major organs.

In the patent art, Tickner, U.S. Pat. No. 4,316,391 discloses an ultrasound technique for measuring blood flow rate. Colley et al., U.S. Pat. No. 4,354,501, discloses an ultrasound technique for detecting air emboli in blood vessels. Numerous patents disclose catheters or probes, including Calinog, U.S. Pat. No. 3,734,094, Wall, U.S. Pat. No. 3,951,136, Mylrea et al., U.S Pat. No. Re. 31,377, Perlin, U.S. Pat. Nos. 4,304,239; 4,304,240 and 4,349,031, Colley et al., U.S. Pat. No. 4,354,501 and Furler, U.S. Pat. No. 4,369,794.

An ideal method would provide for the determination of the cardiac output in a way that is accurate, noninvasive, continuous, inexpensive and suitable for use in those patients whose cardiac output measurement is most critical. The present invention substantially meets such requirements.

SUMMARY OF INVENTION

The primary object of the invention is to provide a method for continuously and accurately measuring cardiac output in a major discharge artery of a mammalian heart, most notably the human heart, without invasion of any closed anatomical cavity or system and without surgery. The lack of invasion of any closed anatomical system and lack of surgery is what is meant by use of the term "non-invasive" in the abstract and in the claims.

The method of the invention comprises placing a sound transducer in great proximity to the ascending aorta of the heart of the mammal by passing a probe carrying the transducer into the trachea and transmitting ultrasound waves from the transducer toward the path of flow of blood in the ascending aorta. The probe can be passed through the nasal or oral cavity, past the epiglottis into the trachea or, in the case of patients who have had a tracheostomy, directly into the trachea through the surgical opening. The reflected ultrasound waves are received by the transducer and the average Doppler frequency difference between the transmitted waves and the reflected waves is measured. The cross-sectional size or area of the ascending aorta at the point of ultrasound reflection is measured and the volumetric blood flow rate is determined from such measurements. The transducer is oriented to transmit and receive ultrasound waves in a direction within the range of 10°–80° with respect to the direction of the path of flow of blood in the ascending aorta.

The apparatus of the invention is a trachael probe comprising a flexible tube of sufficient length to extend from the oral or nasal cavity or from a surgical trachael opening, through the trachea to the bifurcation thereof, with an ultrasound transducer mounted on the tube in proximity to one end and disposed to transmit in a direction within the range of 10°–80° with respect to the axis of the tube. Electrical conductors extend from the transducer the length of the tube. A second transducer can also be mounted on the tube.

DESCRIPTION OF DRAWINGS

FIG. 3 is a horizontal sectional view of the trunk of a human taken at the level of the tracheal bifurcation and shows the close relationship between the trachea and the ascending and descending aorta and the pulmonary arteries.

FIG. 4 is a perspective view of the probe of the present invention with one end cut away in axial section to show the transducer mounting and orientation with respect to the axis of the tube.

FIG. 5 is a schematic view of the trachea and the ascending aorta and shows the location and orientation of the probe and transducers with respect to the path of flow of blood in the ascending aorta.

FIG. 6 is a schematic view and block diagram showing the orientation and relationship of the transducers. The electrical conductors running the length of the tube to the ultrasound generating and receiving device are also shown.

DESCRIPTION OF PREFERRED EMBODIMENT APPARATUS

Figure 1:
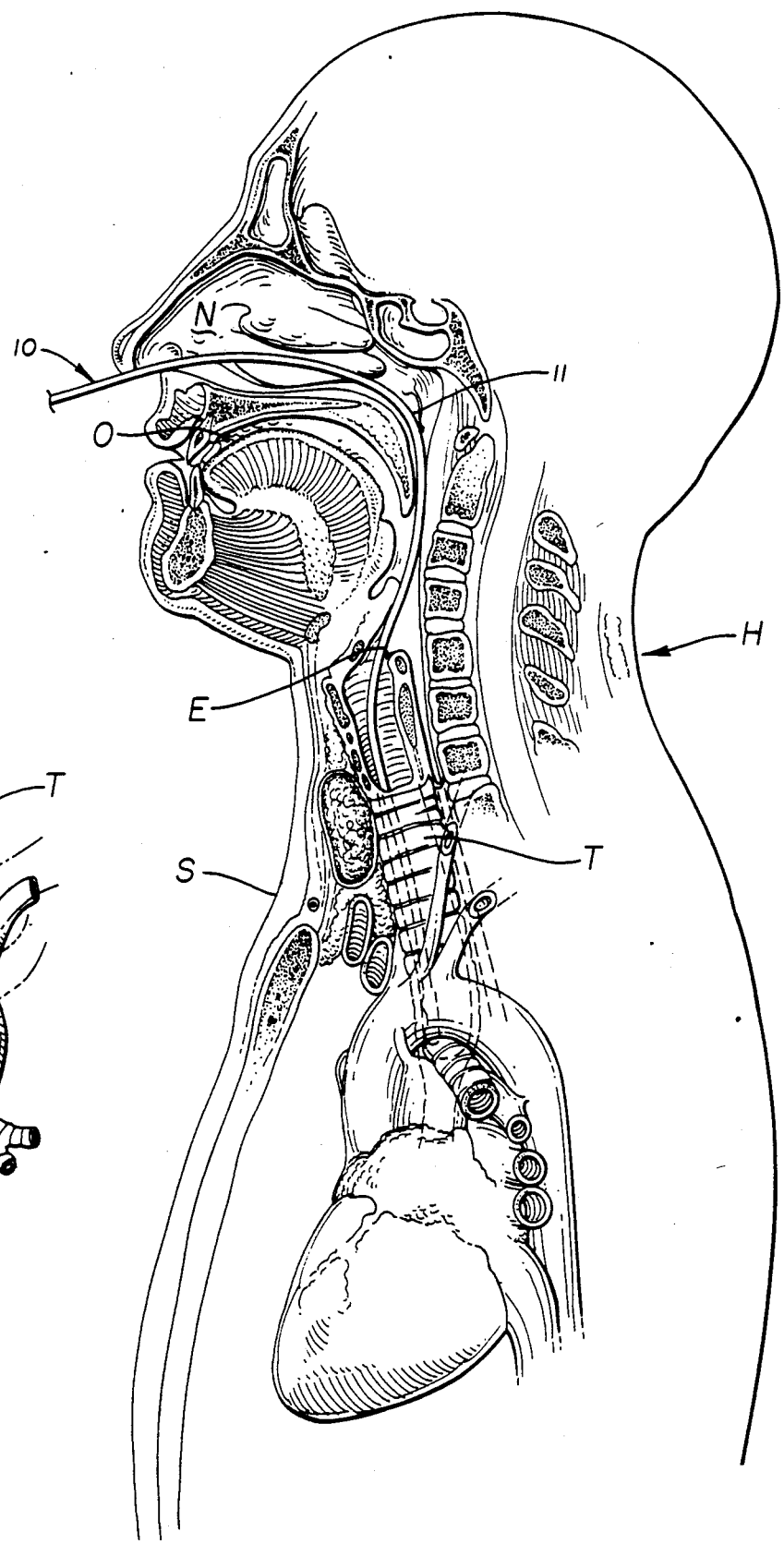
FIG. 1 is a vertical cross-sectional side view of the upper portion of the human body showing the nasal and oral cavities and the pathway through the trachea to the bifurcation thereof. The heart is shown in left lateral or side view. The tracheal probe of the invention is shown in position in the trachea with the transducer(s) in great proximity to the ascending aorta.

The apparatus of the preferred embodiment consists of a probe with a piezoelectric transducer mounted at one end and electrical conductors extending the length of the probe for connection to conventional directional pulsed or continuous wave Doppler ultrasound hardware, such as that described by Hartley et al. in the Journal of Applied Physiology, October 1974 and by Keagy et al. in the Journal of Ultrasound Medicine, August 1983. Modifications to the signal output can be made to display blood flow volume rate, aorta or other vessel diameter, blood velocity and other selected displays.

The probe 10 is shown in FIGS. 1, 4, 5 and 6. Probe 10 consists of flexible plastic tubing 11 roughly three to four feet long and about one-fourth inch in outside diameter. The length must be sufficient to extend from outside the body to the vicinity of the heart through the trachea entering either through the nasal or oral cavity, or through a surgical opening in the case of patients who have had a tracheotomy.

In the preferred embodiment, two piezoelectric transducers 21 and 22 are mounted to the exterior of tube 11 at one end in a mounting medium 23. Transducer 21 is used to collect Doppler data for velocity calculation and transducer 22 is used to collect data for calculation of the diameter of the artery at the point of velocity measurement, although data for diameter measurement can also be collected, though less precisely, using transducer 21. Electrical conductors 24, 25, 26 and 27 extend the length of tube 11 for connection to the conventional Doppler ultrasound hardware 28. Piezoelectric transducers 21 and 22 are directional in ultrasound transmission and are oriented as shown in FIG. 6. Transducer 21 is oriented to transmit and receive ultrasound in a direction 45° with respect to the axis of tube 11, and transducer 22 is oriented to transmit and receive ultrasound in the same plane (i.e. in the plane defined by the axis of tube 11 and the direction of ultrasound transmission from transducer 21) but 90° with respect to the axis of tube 11. The angle of ultrasound transmission from transducer 21 with respect to the axis of tube 11 is designated $\phi$ (See FIG. 6). In the preferred embodiment $\phi$ is 45° but the angle may vary in the range of 10°–80°. Angles less than 10° are not suitable because of the lack of ability to intercept an offset flow path substantially parallel to the axis of tube 11 (which is necessary in the use of the method described in greater detail below), and angles between 80° and 90° are not suitable because the Doppler shift is nonexistent or too small to be useful when the ultrasound waves are reflected by a flow path perpendicular to the direction of the ultrasound transmission. It should also be recognized that piezoelectric transducer 21 can be directed in either direction of the axis of tube 11, i.e., either toward or away from transducer 22, resulting in ultrasound transmission either generally up-stream or generally down-stream of the blood flow path in the artery.

With reference to FIG. 4, lenses 21A and 22A are disposed on the face of transducers 21 and 22, respectively, to provide a medium for the transmission of ultrasound from the transducers to a plane surface at the outermost extremity of the probe structure. This design allows intimate contact between lenses 21A and 22A and the wall of the trachea, T, (see FIG. 5) so that there is no airspace, a barrier to ultrasound transmission, between the wall of the trachea and transducers 21 and 22. An acoustical gel, such as Aquasonic 100, a trademark of and available from Park Laboratories, Orange, N.J. is placed on the surface of lenses 21A and 22A to fill in the small, irregular space or spaces between lenses 21A and 21B and the trachea that remain because of the irregularly shaped and relatively non-deformable cartilaginous inner surface of the trachea when the lenses engage in the trachea. Lenses 21A and 22A may be formed of plastic, such as Plexiglas, a trademark of and available from Rohm and Haas Company, Philadelphia, Pa., and are adhered to transducers 21 and 22, respectively, with any suitable adhesive.

Means is provided to positively locate probe 10 in trachea, T, and to urge lenses 21A and 22B into intimate contact with the inner wall of the trachea. A donut-shaped balloon 29 extends around the periphery of tube 11 above transducers 21 and 22 (See FIG. 4) and, when inflated, helps hold tube 11 in position. A second balloon 30 disposed on one side only of tube 11 opposite transducers 21 and 22, when inflated, urges and holds the transducers in engagement with the wall of the trachea. Balloons 29 and 30 are shown deflated in FIG. 4 and inflated in FIG. 5. Tubing (not shown), which extends the length of tube 11, is provided to inflate and deflate balloons 29 and 30 from a location external of the body when the probe is in place. The operation and use of balloons 29 and 30 is explained in more detail below.

The spacing or distance between transducer 21 and transducer 22 is a function of the angle $\phi$ and the diameter of the vessel, such as the aorta ascending, in which the blood flow measurement is being made, so that the diameter data utilizing transducer 22 and the velocity data utilizing transducer 21 are taken in the same plane across the artery. This insures that the volume computation (velocity x cross-sectional area) is accurate. More specifically, the distance, D, (See FIG. 6) is the estimated diameter, $d_e$, of the vessel at the point of measurement (transducer 22) divided by 2 times the tangent of $\phi$, or $$D = \frac{d_e}{2 \tan \theta}.$$

In the case in which $\phi$ is 45°, as in the preferred embodiment, the distance, D, between transducers is half the estimated diameter (or the radius) of the vessel at the point of diameter and velocity measurement.

Electrical conductors 24, 25, 26 and 27 extend the length of tube 11 and must be capable of transmitting ultra high frequency electrical signals (up to 20 mega Hertz) without significant attenuation. For ease of connection and disconnection of conductors 24-27 to the conventional Doppler ultrasound hardware 28, an electrical connector such as that disclosed in the Furler patent U.S. Pat. No. (4,369,794) can be used.

The foregoing is a description of the preferred embodiment of the tracheal probe 10 that comprises the apparatus of the present invention. A description of the preferred embodiment of the method follows.

METHOD

Figure 2:
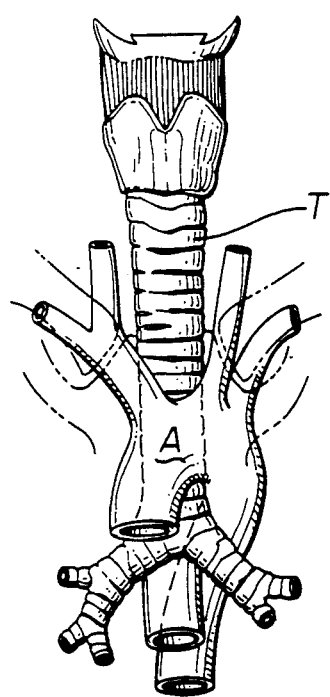
FIG. 2 is a front view of the ascending aorta, the trachea, including the bifurcation thereof, and the esophagus and shows the close relationship between the trachea and the ascending aorta.

An understanding of the method of the present invention requires some understanding of mammalian anatomy and in particular an understanding of the human anatomy, which is shown in pertinent portion in FIGS. 1, 2 and 3. The method is based on the step of locating the ultrasound transducers 21 and 22 in great proximity to the arterial vessel in which blood flow is to be measured, most typically the ascending aorta of a human, without surgery or other invasive techniques. The method relies on the anatomical discovery or fact that the ascending aorta is located adjacent the trachea just above the bifurcation thereof, and that a transducer placed in the trachea can be directed toward the ascending aorta and accurate blood flow measurements made without significant interference. With reference to FIGS. 1, 2 and 3, access to the trachea, T, of a human, H, can be had in accordance with standard medical practice through the nasal cavity, N, or the oral cavity, O, past the epiglottis, E, and into the trachea, T. Access can also be had through a surgical opening at the suprasternal notch, S, in the case of patients who have had a tracheotomy. The ascending aorta, A, and the pulmonary artery, PA, are located in great proximity to the trachea, T, just above the bifurcation, as best seen in FIGS. 2 and 3.

Consequently, a transducer or transducers placed in the trachea as shown in FIG. 1 can be directed to transmit and receive ultrasound waves through the wall of the trachea and through the wall of the ascending aorta or the pulmonary artery to be reflected by the blood flowing in the selected artery and, due to the movement of the blood, cause a Doppler shift in the frequency of the reflected waves as compared to the frequency of the transmitted waves. The ultrasound waves are also reflected by the near and far walls of the artery and such reflection can be used for diameter measurement of the artery.

In accordance with the method of the invention, probe 10 is placed to locate transducers 21 and 22 in the trachea, T, pointing toward the selected artery, such as the ascending aorta, A, as shown in FIG. 5. The position of probe 10 and transducers 21 and 22 can be adjusted until the maximum Doppler shift is obtained and the position can also be checked or confirmed by X-rays to insure placement for optimum data collection. In general, transducers 21 and 22 should be located just above the tracheal bifurcation and directed toward the selected artery, such as the ascending aorta (See FIG. 5).

Balloons 29 and 30 are then inflated with a sufficient minimum pressure to urge the acoustical-gel coated surface of lenses 21A and 22A into intimate contact with the wall of the trachea closest to the ascending aorta. Sufficient minimum pressure is achieved when ultrasound readings are obtained on instrument 28. Balloon 29 positions probe 10 and blocks the annulus between the trachea and probe 10. It is therefore essential that tube 11 serve as a traditional endotracheal tube and have an open end as shown in FIG. 4 to provide for ventilation of the patient through tube 11, which can be regulated and controlled and include the administration of oxygen. Balloon 30 urges and holds the acoustical gelled surfaces of lenses 21A and 22A into intimate contact with the anterior inner wall of the trachea pointing toward the ascending aorta, thereby eliminating an air gap or space between the transducers and the trachea wall, which would be a barrier to ultrasound transmission and reception, and insuring ultrasound transmission from transducers 21 and 22, through lenses 21A and 22A, the acoustical gel, the trachea wall, the connecting tissue that lies between the trachea and ascending aorta, the wall of the ascending aorta, the blood flowing in the ascending aorta and back. It should be noted that there is no airspace between the outside wall of the trachea and the ascending aorta in that all space is filled with connecting tissue, which transmits ultrasound.

In accordance with the methods of the preferred embodiment, after proper placement of probe 10 and connection with the electrical hardware 28, ultrasound signals are generated and the Doppler shift is measured for velocity calculation and data for calculating the diameter of the artery is also collected. These data are used to determine the volumetric rate of blood flow in accordance with the following example.

The average flow velocity $\bar{V}$ of the blood at the point of ultrasound reflection can be determined using the formula:

$$\bar{V} = \frac{C \Delta f}{2 f_o \cos \theta}$$

in which:
$\bar{V}$ = average flow velocity,
C = velocity of sound in the medium (human tissue or blood),
$\Delta f$ = the average Doppler frequency difference or shift,
$\theta$ = the angle between the direction of the transmitted and received waves and the path of flow (velocity vector) of the blood, and
$f_O$ = the ultrasonic carrier frequency (the frequency of transmission).

EXAMPLE OF CALCULATION

Let:
C = 1.55 × 10⁵ cm/sec [Constant for tissue and blood]
$\Delta f$ = 1.5 × 10³ Hz [Measured by Doppler ultrasound]
$f_O$ = 10 × 10⁶ Hz [Assumed primary design frequency], and
$\theta$ = 45° (Cos $\theta$ = 0.7071)
Then:

$$\bar{V} = \frac{(1.55 \times 10^5 \text{ cm/sec}) (1.5 \times 10^3 \text{ Hz})}{2 (10 \times 10^6 \text{ Hz}) (0.7071)}$$

$\bar{V}$ = 16.4 cm/sec [Blood velocity]
The volumetric flow rate, Q, can be determined as follows:

$$Q = VA$$

in which:
Q = Volumetric flow rate
$\bar{V}$ = Average flow velocity
A = Cross sectional area at the point of velocity measurement

EXAMPLE OF CALCULATION

Let:
$\bar{V}$ = V = 16.4 cm/sec
A = $\pi$ r² with r = 1.25 cm [d-measured by ultrasound, r = d/2]
Then:

Q = 16.4 cm/sec × 4.909 cm²
Q = 80.7 cm³/sec or 4.84 liters/minute

In the determination of the area, A, of the artery, transducer 22 is used to collect ultrasound transmission and reflection data from which diameter calculations can be made in conventional manner. For this purpose, transducer 22 is spaced from transducer 21 a distance, D, equal to the estimated diameter, $d_e$ of the artery at the point of measurement divided by 2 times the tangent of $\phi$ so that ultrasound transmissions and reflections from transducer 22 for diameter calculation intersects the velocity ultrasound transmission and reflections from transducer 21 at the center of the artery. Thus the diameter measurement is taken at the point of registration of the average mean velocity of flow in the artery so that the volume calculation is accurate. It should also be mentioned that, for the purpose of calculating the cross sectional area of the artery, the area is assumed to be circular, as is apparent in the foregoing example.

It should be noted that angle $\phi$ is fixed at the time the transducers are mounted on tube 11, assuming no flexing of tube 11 between transducers 21 and 22. In the preferred embodiment the angle $\phi$ is 45°, although as stated above it may range from 10°–80°. Assuming placement of tube 11 in position in the trachea with its axis parallel to the path of flow, P, of blood in the artery in which the measurement is to be taken, the angle $\theta$ (the angle between the direction of ultrasound transmission from transducer 21 and the flow path, P, of blood in the artery) would be the same as the angle $\theta$. It is not always possible, however, to locate tube 11 with its axis precisely parallel to flow path, P. If not positioned parallel to flow path, P, angle $\theta$ will not be the same as angle $\theta$ and, if assumed to be the same unnecessary error will be introduced into the calculation of velocity, $\bar{V}$. To obtain a more accurate value for $\theta$, the following formula can be used:

$$\theta = \cos^{-1} \frac{r_1^2 - r_1 r_2 \cos \phi}{r_1 \sqrt{r_1^2 + r_2^2 - 2 r_1 r_2 \cos \phi}}$$

in which:
$r_1$ = range or distance to artery centerline for transducer
$r_2$ = range or distance to artery centerline for transducer 22
$\theta$ = the angle between transducers 21 and 22.

In the foregoing description two transducers 21 and 22 are disclosed, one for the velocity measurement and one for the diameter measurement. Both the velocity data and the diameter data can be collected using only transducer 21. In such a case the velocity determination is made as described above, and the diameter determination is made by calculating the distance of the hypotenuse, $d_h$, across the artery in the direction of transmission from transducer 21, and calculating the diameter, d, as the hypotenuse times the sin $\theta$ i.e., $d = d_h \sin \theta$. The disadvantage in this procedure is that the diameter determination is not made at the intersection of the ultrasound transmission with the center of the artery, and $\theta$ must be assumed to be the same as $\phi$, which results in some lack of precision in the velocity and volume calculations. Nevertheless, determinations using one transducer only are accurate enough to be useful.

In addition to measuring arterial blood flow rate, the foregoing method can be used during Cardio Pulmonary Resuscitation (CPR) to determine the effectiveness of CPR; to determine blood acceleration as well as flow rate; to obtain a blood velocity profile across the artery, such as the aorta, by range gating; to measure the variation in artery dimension during pulsatile flow; and to obtain a stroke-volume measurement of cardiac output.

A large number of patients who require continuous measurement of cardiac output have significant associated clinical problems. Often such patients have multiple systems organ failure, overwhelming sepsis, significant trauma to many major organ systems, decompensated congestive heart failure, or major myocardial infarction. Such patients often have an endotracheal tube in place because of such problems. For example, in patients having a major surgical procedure, use of general anesthesia requires the presence of an endotrachael tube for the maintenance of the patient's airway. In the case of patients having open heart surgery, an endotrachael tube is often in place for the night following surgery. Patients suffering major trauma are routinely intubated following significant thoracic trauma, significant head injury, or multiple abdominal injuries. Patients in multiple systems organ failure, septic shock, or hemorragic shock have endotracheal tubes in place to assist ventilation during acute decompensation and in the immediate resuscitation phase. Patients with significant burn injuries frequently require endotracheal intubation during initial resuscitation, for transportation to a burn center, and for thermal injury to the respitory system. Patients with decompensated congestive heart failure leading to pulmonary decompensation with pulmonary accumulation of fluid require endotracheal intubation. Such patients may have underlying myocardial infarction, cardiomyopathy, cardiac valvular disease, or chronic congestive heart failure. In many of these examples, stabilization of the cardiovascular system is a prerequisite for removal of the tracheal tube. Consequently, use of an endotracheal probe in accordance with the present invention represents no further invasion of any body cavity. Thus, in the case of patients already having a tracheal tube in place, as well as in patients in which no tracheal tube has been previously placed for other reasons, the method of the present invention provides for measurement of cardiac output at optimum locations without major surgical procedure or invasion of a closed body system. No major body cavity not routinely in communication with the external environment is required. No major or minor surgical procedure is required. No indwelling foreign body is necessary in the vascular system, a major body cavity, or in a major organ. No dye or radioactive substance is necessary for the measurement to be performed, and no air emboli are introduced. Continuous monitoring is also possible.

While the foregoing description of applicants' invention is directed to measurement of cardiac output in the ascending aorta, measurement of blood flow in the descending aorta, the right pulmonary artery and the left pulmonary artery can also be made with the applicants' apparatus.

Having thus described and method and apparatus of the invention the following is claimed.

We claim:

1. A method for determining total cardiac output of a mammalian heart, which comprises:
    a. placing a first sound transducer in proximity to the ascending aorta by passage into the trachea of the mammal,
    b. transmitting ultrasound waves from the first transducer toward the path of flow of blood in the ascending aorta,
    c. receiving the ultrasound waves reflected by the blood,
    d. measuring the average Doppler frequency difference between the transmitted waves and the reflected received waves,
    e. determining the cross-sectonal area of the ascending aorta
    f. determining the volumetric blood flow rate from such measurement and the cross-sectional area of the ascending aorta.

2. The method of claim 1 wherein the ultrasound waves are generated from the first transducer in a direction within the range of 10°–80° with respect to the direction of the path of flow of the blood.

3. The method of claim 1 wherein the ultrasound waves are transmitted from and received by the same transducer.

4. The method of claim 1 wherein the mammal is a human.

5. The method of claim 1 wherein the cross-sectional area is determined by measuring the diameter of the ascending aorta by means of ultrasound wave reflection.

6. The method of claim 5 wherein the diameter of the ascending aorta is determined by placing a second sound transducer in the trachea in proximity to the ascending aorta, transmitting ultrasound waves from the second transducer toward the ascending aorta, receiving the ultrasound waves reflected by the distant wall of the ascending aorta, measuring the time elapsed from transmission to reception, and determining the cross-sectional size of the ascending aorta from such measurements.

7. The method of claim 6 wherein the ultrasound waves from the second transducer are transmitted in a direction 90° with respect to the wall of the ascending aorta.

8. The method of claim 7 wherein the ultrasound waves from the first transducer are transmitted in a direction about 45°, with respect to and intersecting the transmission of ultrasound waves from the second transducer, and the distance between transducers is equal to the estimated radius of the ascending aorta.

9. A method for determining the volumetric rate of flow of blood in the ascending aorta of a human heart, which comprises:
    a. placing a first sound transducer in proximity to the ascending aorta by passage into the trachea,
    b. transmitting ultrasound waves from the transducer toward the path of flow of blood in the aorta in a direction within the range of 10°–80° with respect to the direction of the path of flow,
    c. receiving the ultrasound waves reflected by the blood,
    d. measuring the average Doppler frequency difference between the transmitted waves and the reflected waves,
    e. measuring the diameter of the aorta, and
    f. determining the volumetric blood flow rate from such measurements.

10. The method of claim 9 wherein the ultrasound waves are transmitted from and received by the same transducer.

11. The method of claim 10 wherein the measurement of the diameter of the ascending aorta is done by means of ultrasound wave reflection.

12. The method of claim 11 when the diameter of the ascending aorta is determined by placing a second sound transducer in the trachea in proximity to the ascending aorta, transmitting ultrasound waves from the second transducer toward the ascending aorta, receiving the ultrasound waves reflected by the distant wall of the ascending aorta, measuring the time elapsed from transmission to reception, and determining the cross-sectional size of the ascending aorta from said measurements.

13. The method of claim 12 wherein the ultrasound waves from the second transducer are transmitted in a direction 90° with respect to the wall of the ascending aorta.

14. The method of claim 13 wherein the ultrasound waves from the first transducer are transmitted in a direction about 45° with respect to and intersecting the transmission of ultrasound waves from the second transducer, and the distance between transducers is equal to the estimated radius of the ascending aorta at the point of diameter measurement.

* * * * *